United States Patent
Heiser

Patent Number: 5,890,893
Date of Patent: Apr. 6, 1999

[54] ORTHODONTIC BRACKET

[76] Inventor: Wolfgang Heiser, Dr.-Stumpf-Strasse 73, A-6020 Innsbruck, Austria

[21] Appl. No.: 31,248
[22] Filed: Feb. 26, 1998
[51] Int. Cl.$^6$ ..................................................... A61C 3/00
[52] U.S. Cl. .................................. 433/11; 433/13; 433/14
[58] Field of Search .................................... 433/8, 10, 13, 433/11, 14

[56] References Cited

U.S. PATENT DOCUMENTS

| | | | |
|---|---|---|---|
| 3,871,096 | 3/1975 | Wallshein | 433/11 |
| 4,144,642 | 3/1979 | Wallshein | 433/11 |
| 4,192,070 | 3/1980 | Lemchan et al. | 433/11 |
| 5,356,288 | 10/1994 | Cohen | 433/13 X |
| 5,474,446 | 12/1995 | Wildman et al. | 433/11 X |
| 5,711,666 | 1/1998 | Hanson | 433/11 |

Primary Examiner—Nicholas D. Lucchesi
Attorney, Agent, or Firm—Morgan & Finnegan, LLP

[57] ABSTRACT

An orthodontic bracket having an archwire slot and including a pressure spring capable of exerting a lateral force onto an archwire inserted into the archwire slot, said force pressing the archwire into abutment to a lateral slot wall thereby reducing the clearance of the archwire within the slot.

12 Claims, 8 Drawing Sheets

ORTHODONTIC BRACKET

The invention refers to a bracket for orthodontic treatments, comprising a base plate for attachment to the crown of a tooth and comprising a structure attached to the base plate, elevated over the base plate, said structure having at least one slot for receiving an archwire. Brackets of this kind are generally known and described e.g. in the U.S. Pat. Nos. 5,562,444 (Heiser et al.), 5,074,783 (Reher), 5,022,854 (Broughton) and 4,415,330 (Daisley et al.), the contents thereof are incorporated in this specification by reference.

For the orthodontic treatment of a patient having malposed teeth, the brackets of a complete set of brackets are attached in predetermined positions at the crowns of the teeth of the patient, e.g. by the aid of a cement or adhesive, and subsequently, a common archedly extending archwire is inserted into the archwire slots in the structures of the brackets of a jaw so that the brackets are lined up on the archwire like pearls on a string, see e.g. FIG. 1 in U.S. Pat. No. 4,283,908 (Kurz). The archwire is secured in the slots of the brackets by means of ligatures or my means of closing springs, see e.g. the U.S. Pat. No. 5,562,444 (Heiser et al.).

The brackets are mounted on the crowns of the teeth in a manner that they each have a predetermined orientation with respect to the tooth, see e.g. the U.S. Pat. No. 5,022,854 (Broughton), according to which imaginary prolongation lines of the lateral edges, i.e. sight lines, of the specially formed base plate of the bracket intersect in the tip of the root of the respective tooth. According to the malposition of the teeth of the patient to be overcome, the archwire inserted into the bracket slots at the beginning of the orthodontic treatment has an irregular, more or less waved or angled extension.

Caused by the resiliency of the archwire, the archwire exerts a torque onto the brackets and consequently onto the teeth, which, due to the durability of its influence finally causes the teeth to yield and gradually move to a proper position determined by the orthodontist so that at the end of the orthodontic treatment the archwire connecting the brackets substantially extends in a straight line apart from its arched extension following the arched shape of the jaw.

If the malpositions of the teeth are too great, a relatively thin archwire is sufficient at the beginning of the treatment to cause the required torque at the teeth. An archwire that is too thick would cause an excessive torque. The more the tooth position approaches the proper position, the thicker the archwire must be to exert the torque necessary for moving the teeth. Thus, the archwires are exchanged several times during an orthodontic treatment. However, the brackets are not exchanged. The latter are dimensioned such that the thickest possible archwire can still be received in archwire slots of the brackets.

The movement tolerance or malposition tolerance, that can be comprised by means of an orthodontic treatment of this kind is approximately 15° angle of rotation at the tooth. However, a thin archwire, as it is used at the beginning of the treatment, has a clearance of movement within the slot of each bracket of approximately 8°, so that under certain circumstances an effective angle of rotation of 7° only remains about which the tooth can be rotated by means of said thin archwire. This was taken into account and compensated for by an early exchange of the thin archwire against a thicker one.

The frequent exchange of the archwires is a nuisance for the patient and requires a lot of time, and it is also very expensive because of the medical treatment.

The object of the invention is to provide a bracket of the above-mentioned kind in which the success of the treatment can be improved and the number of archwire exchanges can be reduced.

The invention provides a bracket which has a pressure spring capable of pressing an archwire inserted into the slot transversely to the axis thereof and substantially parallel to the base plate of the bracket in a defined abutment to one of the lateral walls of the archwire slot. Hereby the clearance in the transverse direction, which an archwire of smaller cross sectional dimensions than the bracket slot has within the slot, is compensated or received.

A comparatively thin archwire is therefore capable over a longer period of time compared to the prior art to cause a torque at the brackets which is transferred to the teeth and which leads to an intended movement of the teeth in the direction toward a proper position. The number of archwire exchanges can therefore be reduced compared to the prior art.

The invention can be used for all brackets, no matter how the archwire is secured in the slot against sliding out. Means of that kind can e.g. be ligatures that are wound around the tie wings of the bracket structure and that extend over the archwire, or closing springs, that press onto the archwire from top. "Top" means in this case the side of the bracket opposite the base plate.

In a particular embodiment of the invention, it is even possible to completely refrain from using separate closing springs or ligatures of the above-mentioned kind for securing the archwire within the slot of the bracket. According to said embodiment, the lateral wall of the archwire slot against which the archwire is pressed by the pressure spring, is undercut. The undercut is delimited toward the top by a projection under which the archwire is pressed by the pressure spring and which in cooperation with the spring therefore prevents the archwire from sliding out of the slot.

According to an especially preferred embodiment, the pressure spring, that shall laterally press against the archwire, is a leaf spring, which has two ends and which is clamped into the bracket structure at two positions spaced in the longitudinal direction of the archwire, so that it is curved and projects from the side through an opening in the bracket structure into the archwire slot so far that it can laterally urge against an archwire located in the slot.

The bracket structure in this case is, according to an advantageous embodiment, designed such that the pressure spring can be forced from the described active position by means of a simple, mandrel-shaped tool into a release position that is mirror-inverted thereto, in which it is completely out of the slot.

In an especially preferred embodiment of the invention, a slide plate is used for securing the archwire in the bracket slot, said slide plate being slidably retained at the bracket structure and being capable of being slid over and away from the slot, and said curved leaf spring is mechanically coupled with the slide plate. When displacing the slide plate into the closing position covering the slot, the leaf spring is moved from its release position which is a first stable position over its instable balance point to its active position which is a second stable position, urging against the archwire, in which at the same time it secures the slide plate in its closing position. On the other hand, in the opposite, mirror-inverted bent first position of the leaf spring, it secures the slide plate in its open position, so that the orthodontist may easily insert the archwire into the open archwire slot or may remove it therefrom without any risk that the slide plate moves unintentionally.

The invention can be realized in a very simple manner. When using a leaf spring as a pressure spring, two bearings only have to be formed at the bracket structure between which the leaf spring is clamped.

The invention also enables the orthodontist to influence the torque caused by the archwire at individual teeth individually, i.e. individually for each tooth, in that according to the respective need, it brings the pressure spring into pressure engagement with the archwire (first stable position) or not (second stable position).

The invention will now be described with reference to embodiments shown in the drawings.

Figure 1:
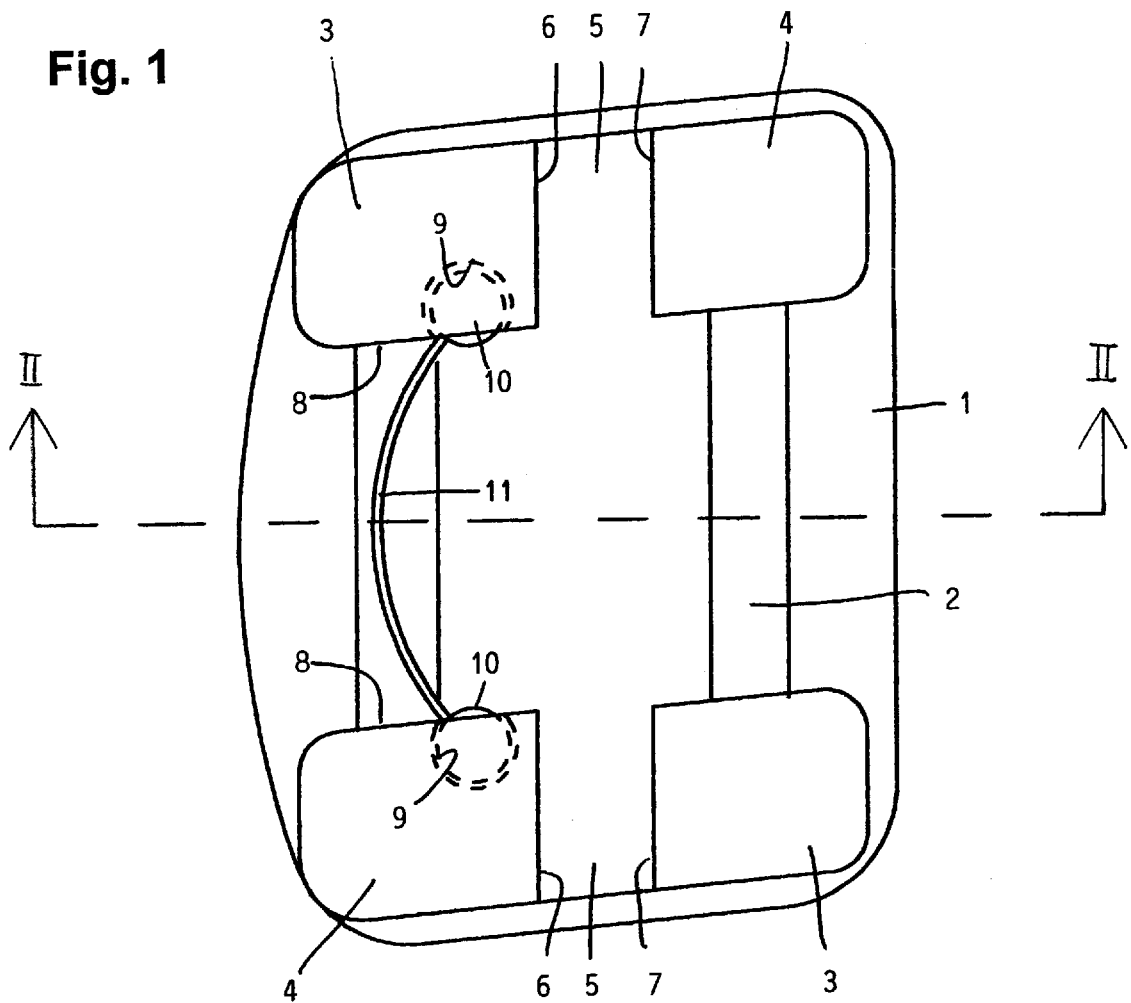
FIG. 1 is a top view onto a bracket according to a first embodiment of the invention in open condition of the pressure spring.
Figure 2:
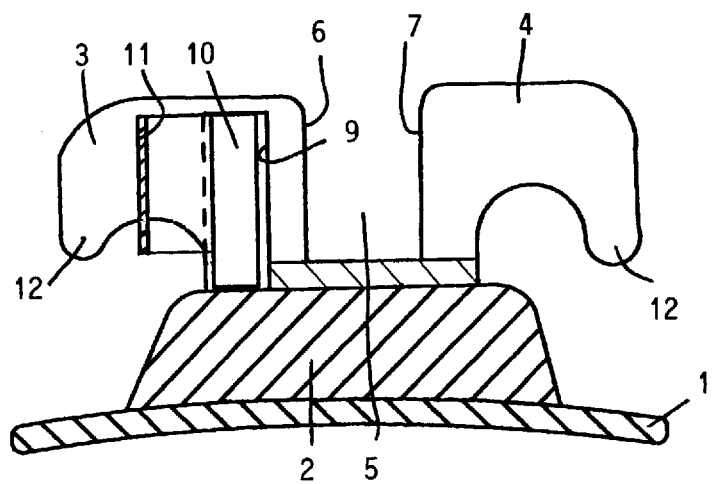
FIG. 2 is a sectional view of the bracket of FIG. 1, cut along the line II—II of FIG. 1.

FIGS. 1 and 2 show a first embodiment of a bracket from the top. On a base plate 1, which is determined for fixing the bracket at the crown of a tooth, a structure is attached, consisting of a base 2, with two pairs of wings 3 and 4 projecting therefrom. The pairs of wings 3, 4 are arranged at a mutual spacing, so that they form a slot 5 between both, which in this case consists of two sections spaced by an opening. The slot 5 serves for receiving an archwire (not shown). Each slot section is limited on both sides by side walls 6 and 7, which form the lateral limitation of the pairs of wings 3 and 4 on sides facing one another.

One bearing 9 each is provided at the two wings 3 of the first pair of wings at the sides facing each other. The ends 10 of a leaf spring 11 are held in these bearings 9, said leaf spring 11 having a total length that is greater than the free distance between the bearings 9. In this manner, the leaf spring 11 mounted in the bearings 9 adopts the arc-like shape shown in FIG. 1 and has two stable conditions, one of which being the open condition shown in FIG. 1. In the other, closed condition, which is shown in FIG. 3, the leaf spring 11 extends in mirror-inverted fashion to the condition of FIG. 1, reflected at an imaginary connection plane extending through the bearings.

The bearings 9 are pocket bores in the embodiment according to FIGS. 1 to 4, which are open at the lateral surfaces 8 of the wings facing one another for penetration of the leaf spring 11 and which were formed, e.g. drilled parallel to one another into the wings from the bottom, i.e. from the side facing the base 2.

Figure 3:
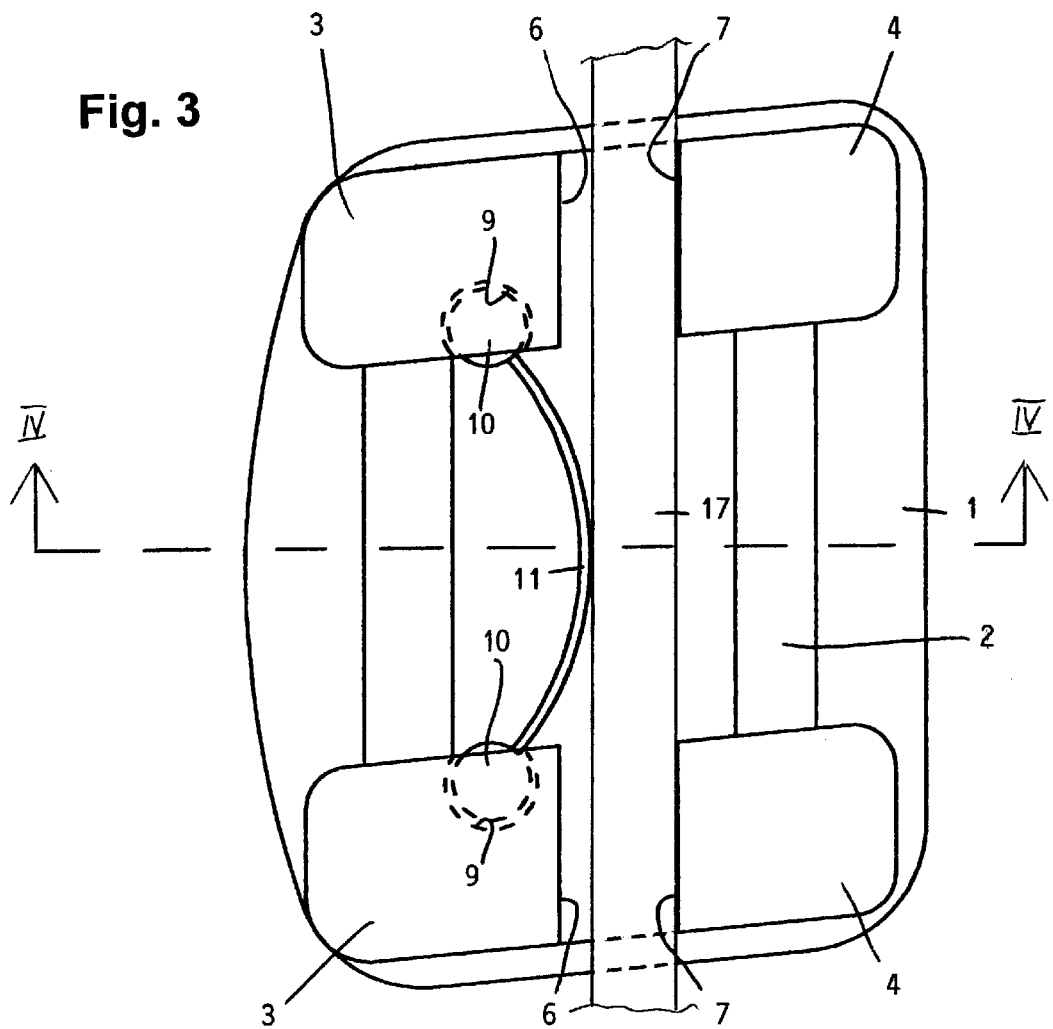
FIG. 3 is a top view onto the bracket of FIG. 1 in closed condition of the pressure spring and with an archwire inserted.
Figure 4:
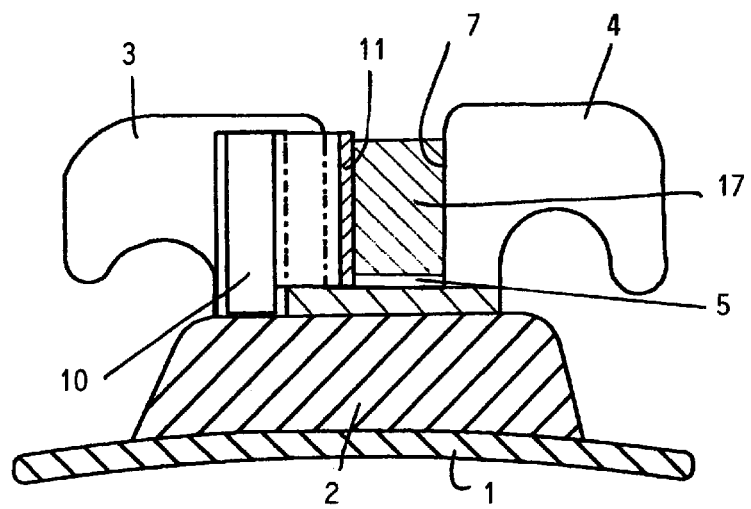
FIG. 4 is a sectional view of the bracket of FIG. 3, cut along the line IV—IV of FIG. 3.

The ends 10 of the leaf spring 11 may be rolled or may be formed to a cylindrical shape by fusing, as is shown in FIGS. 1 and 3. The leaf spring 11 in this embodiment is inserted into the bearings 9 from the bottom, before the base 2 is connected to the pairs of wings. The leaf spring 11 is in this manner irremovably held on the bracket.

Use of this bracket is now explained.

FIGS. 1 and 2 show the bracket in open stable condition of the leaf spring 11. In this first position of the leaf spring, an archwire 17 may be inserted into the slot 5, said archwire being not shown in FIGS. 1 and 2, but may be seen in FIGS. 3 and 4. After inserting the archwire 17 into the slot 5, the leaf spring 11 is brought into a second stable position by the orthodontist by means of a small tool, e.g. a needle, said second position being shown in FIG. 3 and corresponding to the closing position in which the leaf spring 11 presses against the archwire 17, which is why it was previously called "pressure spring", so that the archwire 17 is urged into a defined abutment to the walls 7 of the second pair of wings 4.

Finally, the archwire is secured in the slot 5 for example by winding a ligature (not shown) about the wings 3 and 4 and over the archwire 17. For fixing the ligature to the wings 3 and 4, these wings are provided with downwardly projecting horns, see FIG. 2, which hold the ligature. This feature and the attachment of the ligature are generally known to the person skilled in the art, so that a drawing is not required.

FIGS. 5 to 8 show a second embodiment of the invention, which differs from the first embodiment in that the bracket additionally includes a slide plate 13 which is guided in grooves 14, which are formed closely underneath the upper side in the wings 3 of the first pair of wings. In the wings 4 of the second pair of wings, short grooves 15 are formed in elongation of the grooves 14 in facing sides of these wings 4, see in particular FIG. 6, into which a partial section of the slide plate 13 may penetrate.

The slide plate 13 has lateral flaps 13a, the length of which being dimensioned such that in the closing position of the slide plate 13, the archwire slot 5 of the bracket is fully covered by the slide plate 13. Moreover, the slide plate 13 has a first hole 16 which is adapted for being engaged by a tool, e.g. a needle for displacing the slide plate 13 between its open and closed positions.

Figure 5:
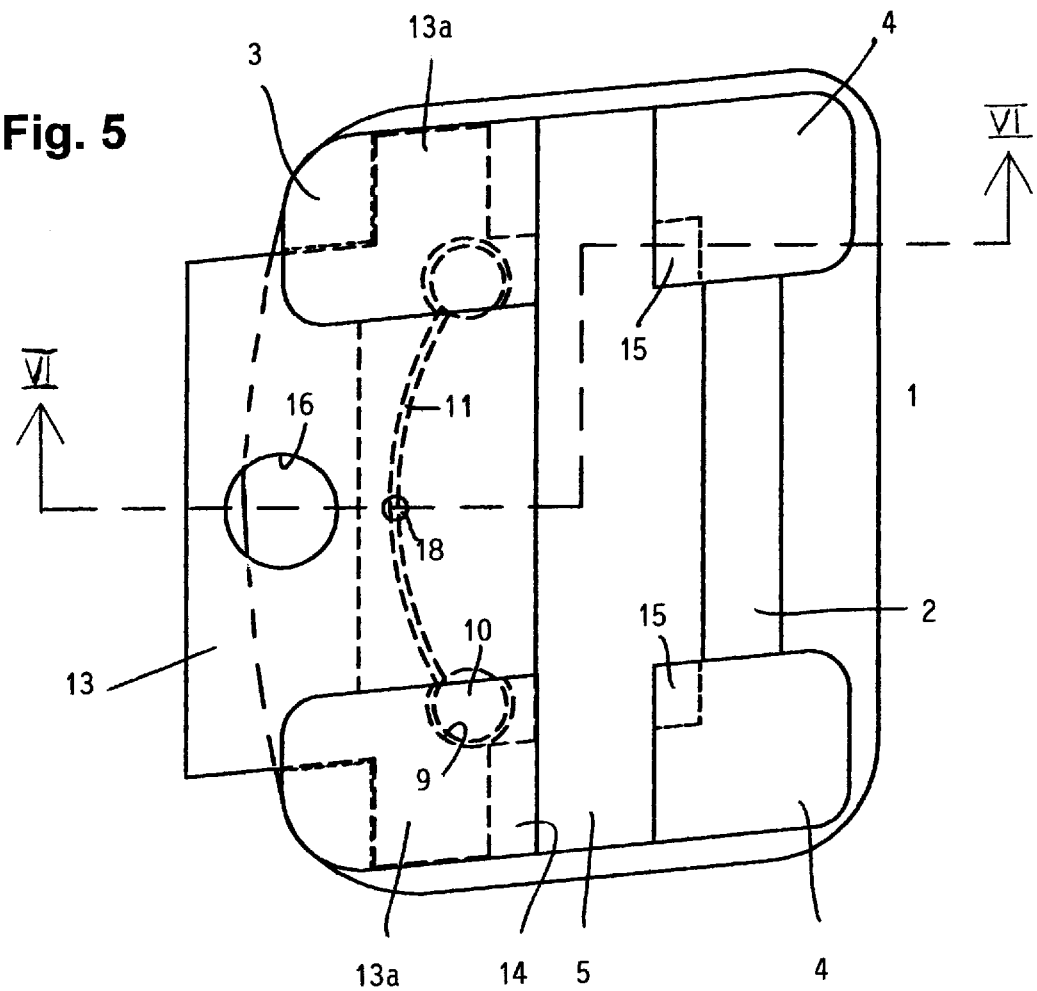
FIG. 5 is a top view onto a bracket according to a second embodiment of the invention in open condition of the pressure spring.
Figure 6:
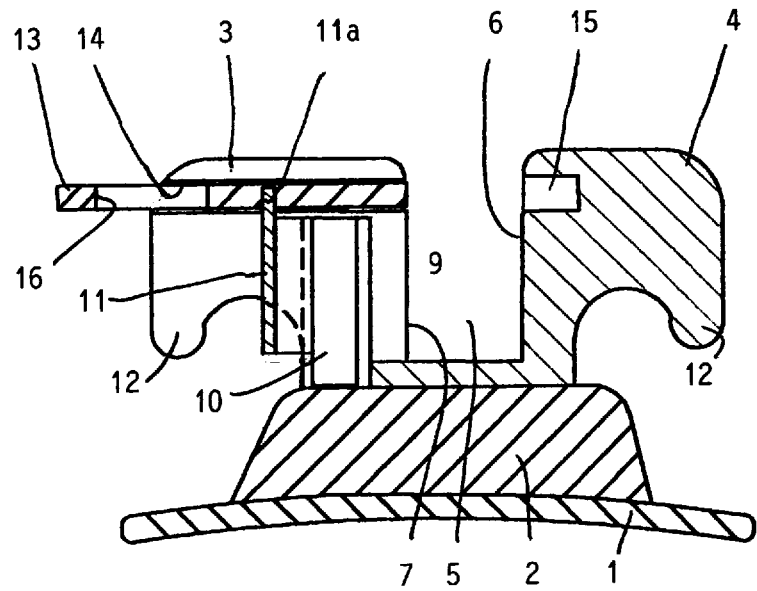
FIG. 6 is a sectional view of the bracket of FIG. 5, cut along the line VI—VI of FIG. 5.

FIGS. 5 and 6 show the slide plate 13 and the leaf spring 11 in open condition, in which the archwire slot 15 is fully exposed. In the area located underneath the center of the leaf spring 11, the slide plate 13 has a second, small hole 18, into which a projection 11a formed at the leaf spring 11 engages, which couples the leaf spring 11 with the slide plate 13, see FIG. 6.

Figure 7:
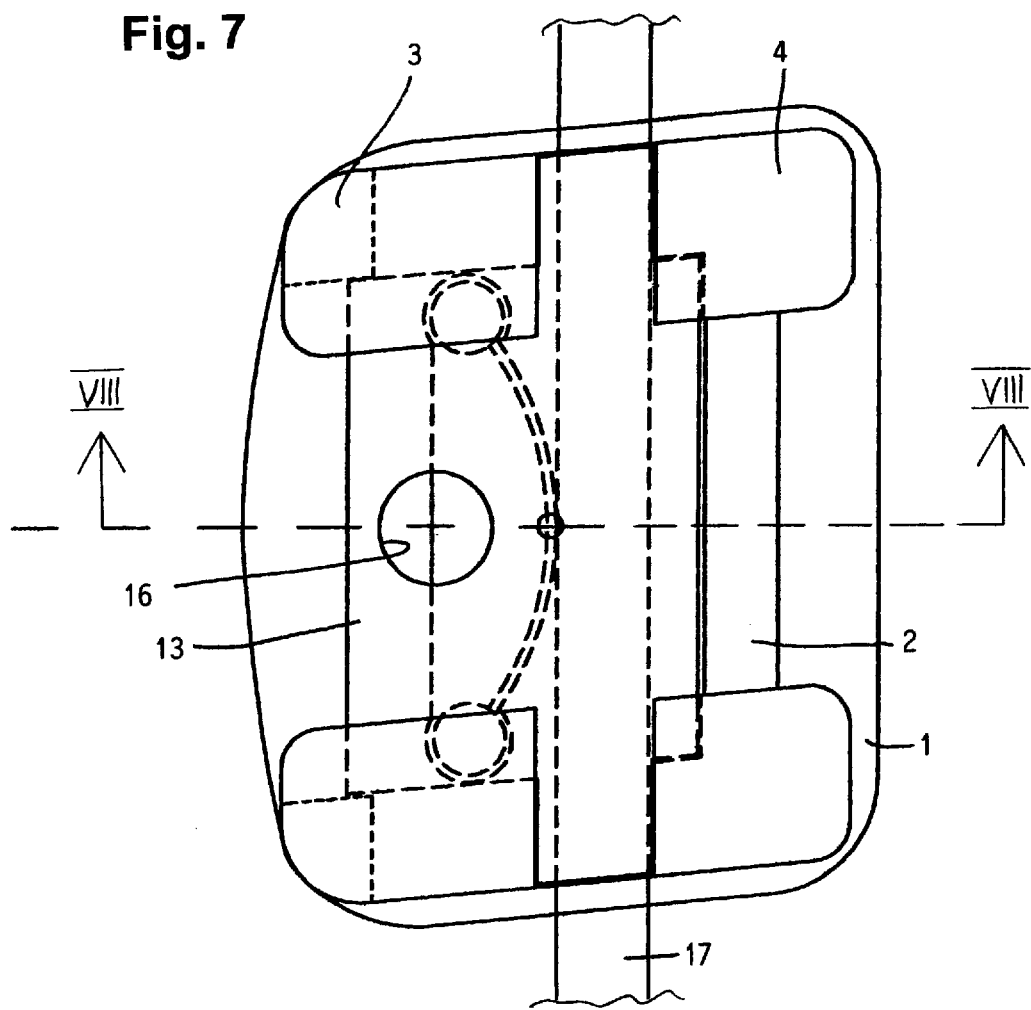
FIG. 7 is a top view onto the bracket of FIG. 5 in closed condition of the pressure spring with an inserted archwire.
Figure 8:
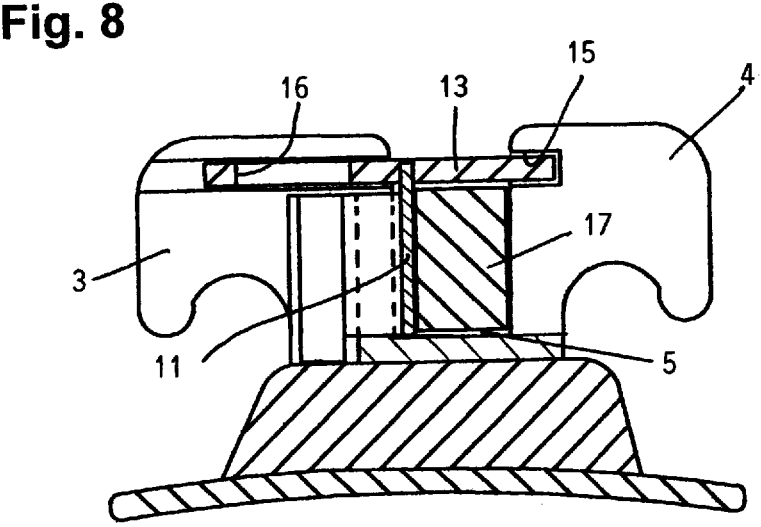
FIG. 8 is a sectional view of the bracket of FIG. 7, cut along the line VIII—VIII of FIG. 7.
Figure 9:
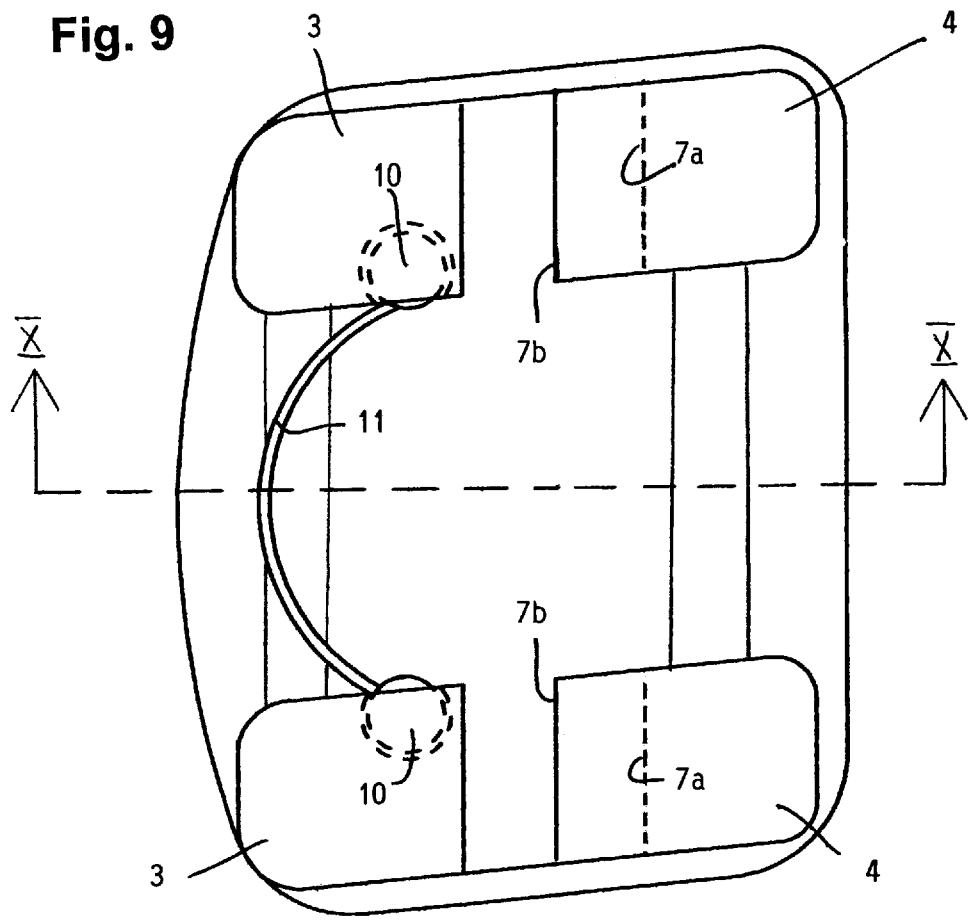
FIG. 9 is a top view onto a bracket according to a third embodiment of the invention in open condition of the pressure spring.
Figure 10:
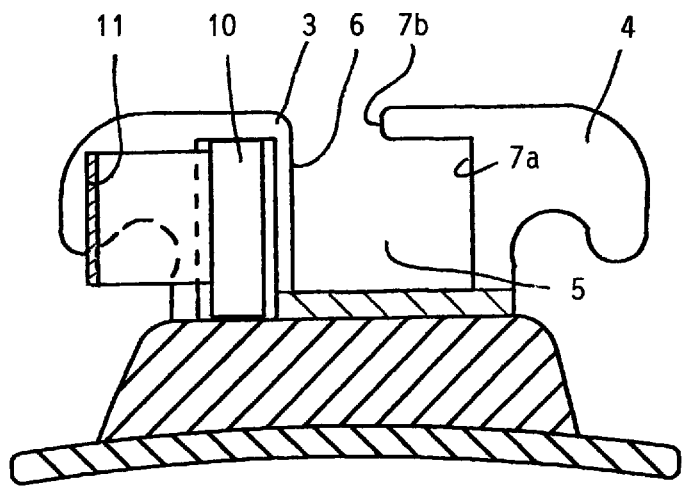
FIG. 10 is a sectional view of the bracket of FIG. 9, cut along the line X—X of FIG. 9.

By means of a tool, e.g. a needle, which is inserted into the hole 16, the slide plate 13 may be brought into the closing position shown in FIG. 7 in which it fully covers the archwire slot 5 and secures an archwire 17 inserted into the slot 5. The front section of the slide plate 13 penetrates into the short grooves 15 at the wings 4 of the second pair of wings. By the coupling of the leaf spring 11 with the slide plate 13, the leaf spring 11 is brought into its second stable position, the closing position, as shown in FIG. 7, in which it also secures the slide plate 13.

The slide plate 13 may consist of metal, it does not have to be resilient and could thus also be made of ceramics. The use of the slide plate 13 renders the use of ligatures superfluous, since the slide plate 13 secures the archwire within the slot 5 against sliding out.

FIGS. 9 to 12 show a third embodiment of the invention, which is very similar to the first embodiment. It differs from the first embodiment in that the wings 4 of the second pair of wings have an undercut 7a on the side wall opposite to the leaf spring 11, said undercut being limited toward the top by a projection 7b.

Figure 11:
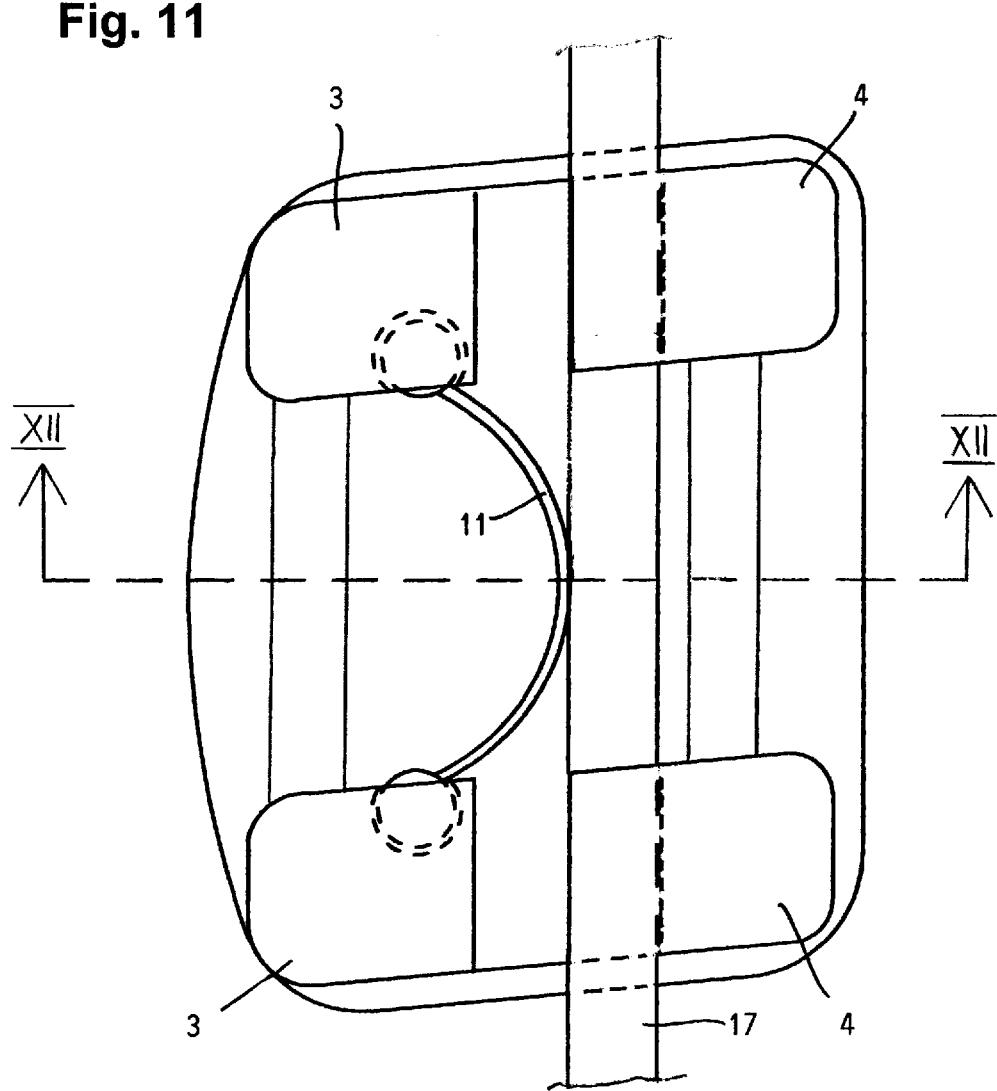
FIG. 11 is a top view onto the bracket of FIG. 9 in closed condition of the pressure spring and with an inserted archwire.
Figure 12:
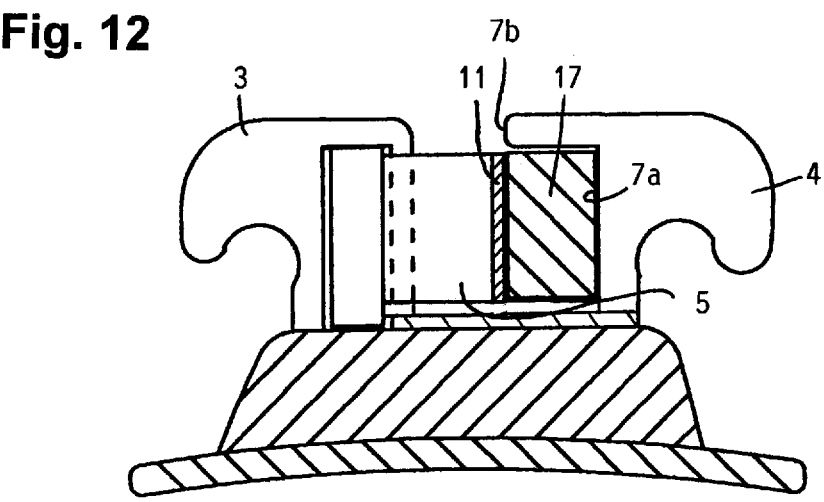
FIG. 12 is a sectional view of the bracket of FIG. 11, cut along the line XII—XII of FIG. 11.
Figure 13:
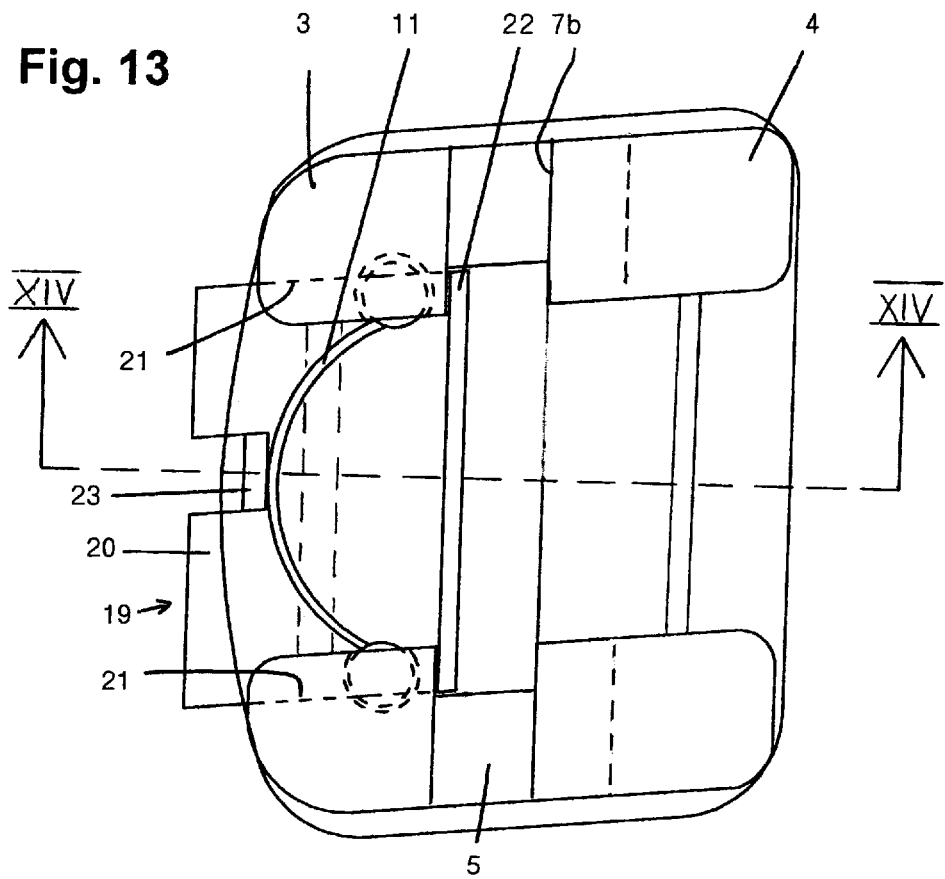
FIG. 13 is a top view onto a fourth embodiment of the invention in open condition of the pressure spring.
Figure 14:
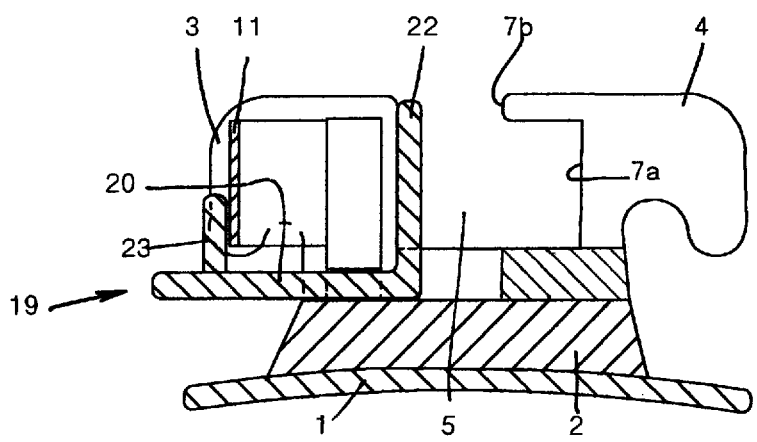
FIG. 14 is a sectional view of the bracket of FIG. 13, cut along the line XIV—XIV of FIG. 13.
Figure 15:
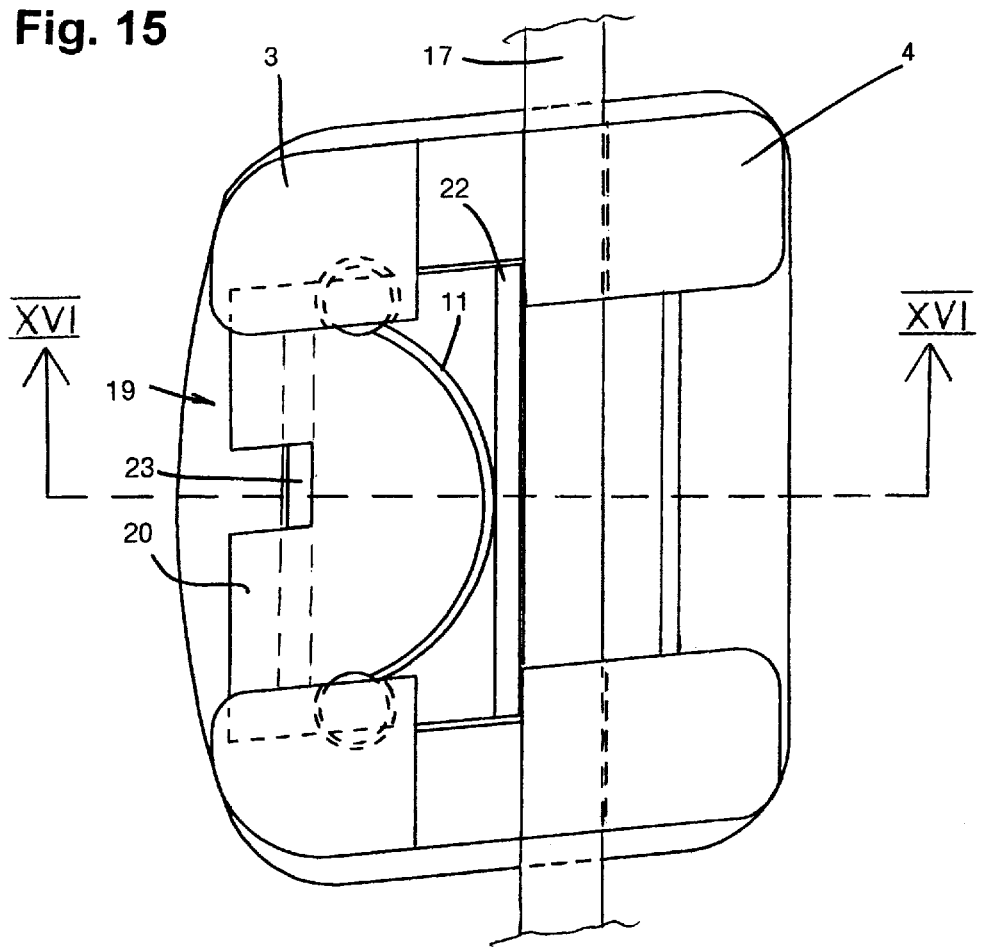
FIG. 15 is a top view onto the bracket of FIG. 13 in closed condition of the pressure spring.
Figure 16:
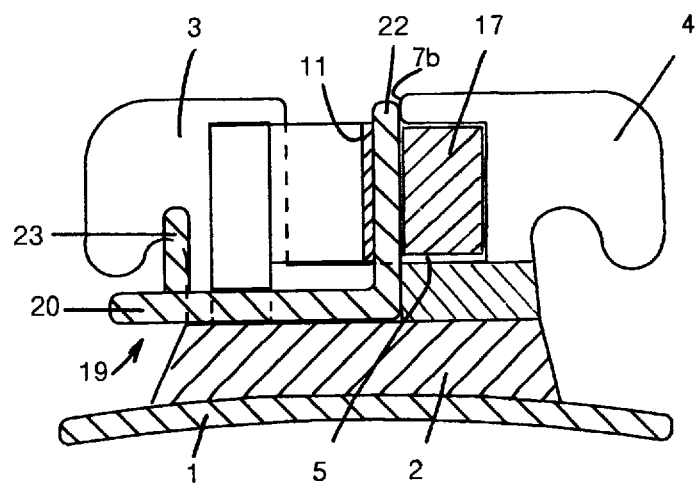
FIG. 16 is a sectional view of the bracket of FIG. 15, cut along the line XVI—XVI of FIG. 15.

As can be learned from FIGS. 11 and 12, in which an archwire 17 of a rectangular cross section inserted into the bracket is shown, the archwire is urged underneath the projection 7b into abutment with the undercut in the closing position of the leaf spring 11, so that the archwire is held by the projection 7b in cooperation with the leaf spring 11 in the slot 5 of the bracket. In this embodiment it can therefore be refrained from using ligatures or a slide plate or other means for securing the archwire 17.

FIGS. 13 to 16 show a further embodiment of the bracket of FIGS. 9 to 12. This bracket differs from that of FIGS. 9 to 12 in that the bracket of FIGS. 13 to 16 additionally comprises a bent slider 19 extending in parallel to the archwire slot 5 and having a length to span the lateral opening between the wings of both pairs of wings 3 and 4.

Said slider 19 has an L-shaped cross section. One of the flanges, referenced 20, of said slider 19 extends essentially in parallel to the base plate 1 and is slidably guided within grooves 21 formed in the wings 3 of the first pair of wings at the sides facing each other. The other flange, referenced 22, of said slider 19 extends normal to said first mentioned flange 20 and is adapted to be engaged and urged towards the other pair of wings 4 by said leaf spring 11 in the second position thereof.

The flange 20 first mentioned above comprises a tab 23 cut out from the rear edge of said flange and bent upwardly. Said tab 23 is adapted to be engaged by a tool (not shown) for displacing the slider 19 into the closing and open positions and further is adapted to be engaged by the leaf spring 11 in its first (open) position (see FIG. 15) to secure the slider 19 in its open position, comparable to the slider plate 13 in the embodiment of FIGS. 5 to 8.

The slider 19 is made of a rather rigid material. Thus, in view of its length, the slider 19 is able to distribute the force exerted locally only by the leaf spring 11 onto its flange 22 in the second position of the leaf spring onto a considerable length of the archwire 17 disposed in the slot 5, thereby additionally reducing the clearance which may still exist between the archwire and the side wall 7a of the second pair of wings 4. Further, flange 20 of slider 19 due to its length additionally helps securing the archwire in its position under the projections 7b against accidental escape.

I claim:

1. An orthodontic bracket comprising a base plate for attachment to a crown of a tooth and a structure secured to an upper side of the base plate and raising over the base plate, said structure comprising at least one slot open toward a top of said bracket and limited by a bottom wall and side walls and which is adapted to receive an archwire, wherein a pressure spring is supported at the bracket which is adapted for causing a force at an archwire inserted into the slot, said force acting in the direction towards one of the side walls limiting the slot, said pressure spring being an arc-shaped leaf spring, the ends of which are supported in recesses formed in the bracket at positions spaced along the slot.

2. A bracket according to claim 1, wherein the recesses are laterally open bores extending upwards from a side of the structure directed against the base plate.

3. A bracket according to claim 2, wherein the bores are pocket bores each of which being closed at an upper end thereof.

4. A bracket according to claim 2, wherein the leaf spring has enlargements formed at the leaf spring's end by rolling or fusing, said enlargements being accommodated in the bores.

5. A bracket according to claim 3, wherein the leaf spring has enlargements formed at the leaf spring's end by rolling or fusing, said enlargements being accommodated in the bores.

6. A bracket according to one of claims 1 and 2 to 5, wherein the structure of the bracket has an opening at both sides of the slot, so that the structure forms two pairs of wings which laterally limit the slot, and the leaf spring is clamped between the wings of one of the pair of wings.

7. A bracket according to claim 6, wherein a slide plate is displaceably supported at the bracket, said slide plate being movable into a position covering the slot and being mechanically coupleable to the leaf spring.

8. A bracket according to one of claims 1 and 2 to 5, wherein a slide plate is displaceably supported at the bracket, said slide plate being movable into a position covering the slot and being mechanically coupleable to the leaf spring.

9. A bracket according to one of claims 1 and 2 to 5, wherein the side of the structure opposite the pressure spring comprises an undercut which is limited in a direction opposite to the base plate by a projection which is adapted to hold an archwire inserted into the slot.

10. A bracket according to claim 9, further comprising a bent slider having a first flange slidably guided in grooves provided at the structure at positions facing each other and having a second flange normal to said first flange, said second flange being adapted to be engaged by the pressure spring so as to be laterally urged against an archwire inserted into the slot and held therein by said projection.

11. A bracket according to claim 10, wherein the first flange of the bent slider comprises a cut out at the edge opposite the second flange, said cut out forming a tab which is bent upwardly.

12. A bracket according to claim 11, wherein said spring is an arc-shaped leaf spring the ends of which being supported in recesses formed at the bracket at positions spaced along the slot, said leaf spring having a first stable position in which the apex of said leaf spring is distal from the slider second flange and engages said slider tab, and a second stable position in which the apex of said leaf spring engages said slider second flange.

* * * * *